(12) United States Patent
Märzendorfer

(10) Patent No.: US 7,844,095 B2
(45) Date of Patent: Nov. 30, 2010

(54) METHOD AND APPARATUS FOR VIRTUAL BOWEL CLEANING

(75) Inventor: Walter Märzendorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 994 days.

(21) Appl. No.: 11/652,030

(22) Filed: Jan. 11, 2007

(65) Prior Publication Data
US 2007/0297662 A1  Dec. 27, 2007

(30) Foreign Application Priority Data
Jan. 12, 2006  (DE) .................... 10 2006 001 655

(51) Int. Cl.
*G06K 9/00* (2006.01)
(52) U.S. Cl. .................. 382/131; 382/173; 382/260; 382/309
(58) Field of Classification Search .................. 382/131
See application file for complete search history.

(56) References Cited

U.S. PATENT DOCUMENTS

| | | | |
|---|---|---|---|
| 6,331,116 B1 | 12/2001 | Kaufman et al. | |
| 6,947,784 B2* | 9/2005 | Zalis ........................... | 600/425 |
| 7,050,533 B2* | 5/2006 | Heismann et al. ............. | 378/53 |
| 7,158,611 B2* | 1/2007 | Heismann et al. .......... | 378/98.9 |
| 7,209,536 B2* | 4/2007 | Walter et al. ................... | 378/5 |
| 7,599,465 B2* | 10/2009 | Walter et al. ................... | 378/4 |
| 7,680,313 B2* | 3/2010 | Gundel ........................ | 382/131 |
| 7,747,055 B1* | 6/2010 | Vining et al. ............... | 382/131 |
| 2002/0097320 A1* | 7/2002 | Zalis ........................... | 348/65 |
| 2005/0084063 A1* | 4/2005 | Heismann et al. ............. | 378/53 |

(Continued)

FOREIGN PATENT DOCUMENTS

DE  101 43 131 A1  4/2003

(Continued)

OTHER PUBLICATIONS

Lakare, S.; Ming Wan; Sato, M.; Kaufman, A.; , "3D digital cleansing using segmentation rays," Visualization 2000. Proceedings, vol., No., pp. 37-44, Oct. 13-13, 2000.*

(Continued)

*Primary Examiner*—Sath V Perungavoor
(74) *Attorney, Agent, or Firm*—Harness, Dickey & Pierce, P.L.C.

(57) ABSTRACT

A method and an apparatus for virtual bowel cleaning are disclosed. A first CT volume data record of an area of the bowel of interest is produced, in which voxels relating to a bowel content are identified and are suitably modified in order to obtain a modified data record without visible bowel contents, which is then visualized. In at least one embodiment of the method, at least one further volume data record is produced of the area of interest, which was recorded by a CT scanner with a different spectral distribution than the first volume data record which was recorded by a CT scanner, with at least some of the voxels relating to the bowel content being identified on the basis of information about a local density and/or atomic number, which is obtained from data in the first and the further volume data record taking account of the different spectral distributions. In at least one embodiment, the method and the apparatus make it possible to increase the reliability of virtual bowel cleaning.

8 Claims, 2 Drawing Sheets

U.S. PATENT DOCUMENTS

| | | | |
|---|---|---|---|
| 2005/0256399 A1 | 11/2005 | Sirohey et al. | |
| 2006/0109953 A1 | 5/2006 | Walter et al. | |
| 2007/0073114 A1* | 3/2007 | Gundel | 600/300 |
| 2007/0116346 A1* | 5/2007 | Peterson et al. | 382/131 |
| 2007/0297662 A1* | 12/2007 | Marzendorfer | 382/131 |

FOREIGN PATENT DOCUMENTS

| | | |
|---|---|---|
| DE | 103 47 971 B3 | 6/2005 |
| DE | 10 2005 055 389 A1 | 5/2006 |

OTHER PUBLICATIONS

B.J.Heismann et al.: „Density and atomic number measurements with spectral x-ray attenuation method, Journal of Applied Physics, vol. 94, No. 3, Aug. 2003, pp. 2073-2079.

Remy W.F.Geenen et al.: "CT and MR Colonography: Scanning Techniques, Postprocessing, and Emphasis on Polyp Detection", RadioGraphics 2004, vol. 24 : 18e, published online Oct. 3, 2003.

B.Wang et al.: "Quantitative Diagnosis of Fatty Liver with Dual-Energy CT—An experimental study in rabbits", Acta Radiologica, vol. 44, 2003, pp. 92-97.

Invention Report, 2005.

German Office Action, 2006.

* cited by examiner

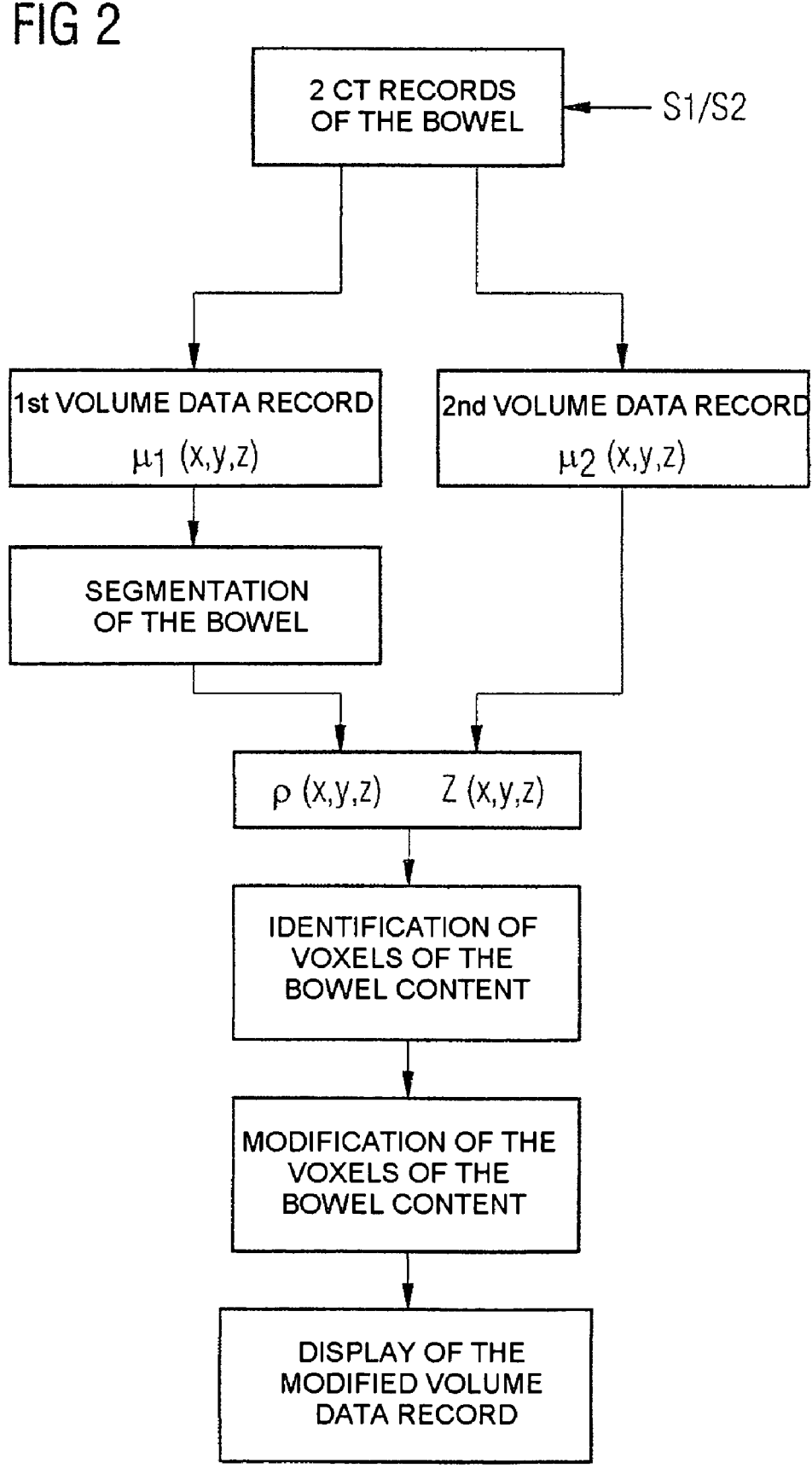

METHOD AND APPARATUS FOR VIRTUAL BOWEL CLEANING

PRIORITY STATEMENT

The present application hereby claims priority under 35 U.S.C. §119 on German patent application number DE 10 2006 001 655.6 filed Jan. 12, 2006, the entire contents of which is hereby incorporated herein by reference.

FIELD

Embodiments of the present invention generally relate to a method and/or an apparatus for virtual bowel cleaning. For example, it may relate to one by which a volume data record which is recorded by a CT scanner of at least one area of interest of the bowel is produced, voxels relating to the bowel content are identified and suitably modified in the first volume data record or in a data record derived from it, in order to obtain a modified data record without any visible bowel content, and the modified data record is visualized.

BACKGROUND

In addition to endoscopy and conventional X-ray colonography, virtual CT colonography or CT colonoscopy derived from it is becoming significantly important. Bowel cancer represents a frequent cause of death in western countries. One good indicator of this illness is polyps which are formed a relatively long time before the outbreak of bowel cancer in the bowel. In many cases, these develop over a number of years to form malign carcinomas.

One effective measure against bowel cancer is thus early identification of polyps. In the past, endoscopic methods were used for this purpose. Recently, the technique of virtual colonography has become important, in which the bowel is scanned by means of a CT scanner (CT) or a magnetic resonance imaging scanner (MRI) and the images obtained during this process are then analyzed at medical workstations.

In the case of virtual colonography, the bowel must be cleaned by way of suitable medication before the examination, in order to make it possible to identify structures which indicate polyps or other conspicuous features on the bowel wall in the later images. Patients find this to be unpleasant, and it therefore frequently represents an obstacle to the examination.

The technique of so-called virtual bowel cleaning is also known, in addition to this actual bowel cleaning. In the case of this virtual bowel cleaning, the volume data record of the bowel as recorded using a CT scanner is subjected to post-processing in which voxels which relate to the bowel content are identified in the volume data record and are eliminated by digital subtraction from the volume data record. The delineation of the bowel and bowel content required for this purpose is made easier by the introduction of contrast agents. These contrast agents are either added to the food which the patient consumes in a time period before the examination, or are given to the patient intravenously immediately before the examination.

The first situation results in contrasting of the bowel content, while the second case results in contrasting of the bowel with respect to the bowel content. In addition, before the examination, the bowel is expanded by pumping in surrounding air or $CO_2$ gas in order to allow it to be displayed better. Those voxels in the volume data record which relate to the bowel content are in this case identified on the basis of the CT attenuation volumes of these voxels, or on the basis of changes in the CT attenuation values between mutually adjacent areas. Both are known, for example, from U.S. Pat. No. 6,331,116 B1, which discloses a method of this generic type for virtual bowel cleaning.

Despite all the known techniques, residual stool in the bowel always results in problems relating to delineation from the tissue, in particular from the bowel wall. One conventional strategy is to carry out the examination first of all lying on the back and then once again lying on the stomach, in the hope that the location of the bowel contents would change during the process, in this way identifying the contents as stool. However, this is not always successful.

SUMMARY

In at least one embodiment of the present invention, a method and/or an apparatus is specified for virtual bowel cleaning, in which reliable delineation is achieved between the bowel content and the bowel.

In the case of at least one embodiment of the present method for virtual bowel cleaning, a first volume data record is produced of at least one area of interest of the bowel which has been recorded by a CT scanner with a known spectral distribution. The voxels relating to the bowel content are identified and suitably modified in the first volume data record or in a data record which has been derived from it, for example by segmentation of the bowel, in order to obtain a modified data record without any visible bowel content. This can be done by subtraction of the CT attenuation value of the respective voxel at this point, or by resetting the CT attenuation value of the respective voxel to a constant value, for example to the value of air in which (C=−1000 HU).

The modified data record obtained in this way, in which the voxels relating to the bowel content have been eliminated, that is to say they appear dark in the image display, is then visualized in the desired manner. The profile of the bowel wall can thus be seen in the resultant image without any disturbing bowel content, so that structures which indicate polyps or other conspicuous features on the bowel wall can be identified better. This visualization may, for example, be an MPR (multi-planar reformatting) display or a display based on an endoscopic perspective (virtual colonoscopy). The user can, of course, choose any type of display, as required.

At least one embodiment of the present method is distinguished in that at least one further volume data record is produced of the area of interest, which is being recorded by the CT scanner with a different known spectral distribution than the first volume data record, with at least some of the voxels relating to the bowel content being identified on the basis of information about a local density and/or atomic number, which is obtained from the data in the first and the further volume data record taking account of the different known spectral distributions.

In at least one embodiment of the present patent application, the generally chosen expression CT attenuation value denotes not only the attenuation coefficient μ but also the CT value C, since the two can be transformed to one another without any problems. Furthermore, in the context of this description, the expression atomic number is not used in the strict element-related sense but, instead of this, denotes an effective atomic number of a tissue or material, which is calculated from the chemical atomic numbers or anatomic weights of the elements included in the structure of the tissue or of the material.

In at least one embodiment of the present method, information about the density ρ and atomic number Z of the material being examined at the location of the respective voxel under consideration is used to distinguish better between bowel content and bowel wall, and this information can be obtained from examination with at least two different spectral distributions.

In computed tomography, the spatial distribution of the position-dependent, energy-dependent and possibly time-dependent attenuation coefficients in the object being examined is displayed. The magnitude of the attenuation coefficients for a specific energy is dependent on the atomic number Z and the density ρ of the material being examined.

It is known that a two-point measurement with different energies and/or different spectral distribution (two-spectra or multiple-spectra CT) allows density to be determined. Examples relating to this can be found, for example, in DE 101 43 131 A1, in DE 103 47 971 B3 or in the article by B. J. Heismann et al., "Density and atomic number measurements with spectral X-ray attenuation method", Journal of Applied Physics, Volume 94, Number 3, 2003, pages 2073 to 2079, each of whose disclosure content relating to the procedure for calculation of the local densities and/or atomic numbers is incorporated herein the present patent application by reference.

In at least one embodiment of the present method, this additional information which is obtained by way of the at least two volume data records recorded with different spectral distributions and which relates to the local density and/or atomic number is used in order to make it possible to distinguish better between the bowel content and the bowel wall and/or tissue in the first volume data record.

The method in this case makes it possible to identify all of the voxels relating to the bowel content on the basis of the information about the local density and/or atomic number. However, it is also possible to first of all carry out an initial identification process using the CT attenuation values, in order subsequently to additionally make use, only in the transitional areas between the bowel wall and the bowel content, of the density information and/or of the information relating to the atomic number, for reliable identification and better differentiation.

The entire process can be carried out in a completely automated manner by suitable presetting of threshold values for the attenuation values, the density and the atomic numbers. The additional information results in the method leading to more reliable delineation between bowel content and bowel wall, so that the image of the bowel as displayed after virtual bowel cleaning can also be assessed more reliably.

The method can be used with all conventional modern methods for CT colonography and CT colonoscopy. The patient can thus, of course, still be given a laxative before the examination, in order to at least partially empty the bowel. Remaining stool can then be identified by way of the information relating to the density and/or atomic number using at least one embodiment of the present method, in order to eliminate from the volume data record those voxels which relate to the remaining stool. In this case, it is not absolutely essential to give a contrast agent.

Furthermore, the patient can also be prepared by giving contrast agent orally or rectally, so that the virtual bowel cleaning can the be carried out with better identification of the stool to which contrast agent has been added, in conjunction with the information relating to the density and/or atomic number. At least one embodiment of the present method can also be carried out in conjunction with preparation of the patient by way of contrast agent being given intravenously, in which case the identification of stool delineated from tissue to which contrast agent has been added is also improved by two-spectra or multiple-spectra CT in this case.

It is also still possible to carry out the examination with the patient in two different positions, lying on the back and lying on the stomach. In this case, by way of example, two successive complete CT records can be produced, firstly in the first position using the first energy spectrum, and secondly in the other position using the second energy spectrum.

The two volume data records with different spectral distributions can be obtained by two successive complete CT records which, for example, have been recorded with different tube voltages being applied to the X-ray tube. CT scanners with a plurality of X-ray sources or with a plurality of detector systems which have different spectral sensitivity can, of course, also be used. In principal in the case of at least one embodiment of the present method, the different spectral distribution can be achieved not only by a different spectral distribution of the emitted X-ray radiation but also by different spectral sensitivity of the X-ray detectors used, or by a combination of both. It is also possible to use suitable filters in order to produce the different spectral distributions. By way of example, the method can thus also be carried out with a single emission spectrum from the X-ray source, by using energy-resolving detector systems.

Furthermore, it is also possible to use more than two volume data records in order to determine the local density and/or atomic number, in which case each further volume data record is then recorded with a spectral distribution which differs from the other volume data records. This procedure makes it possible to improve the accuracy of determination of the density and/or atomic number.

If a contrast agent is used, this is preferably chosen such that its density and/or atomic number parameters differ as much as possible from the density and/or atomic number of the tissue (if given orally or rectally) or from the density and/or atomic number of the bowel content (if given intravenously). This further improves the reliability of the identification of the bowel content in at least one embodiment of the present method. In addition and independently of this, at least one embodiment of the present method makes it possible to dispense with the preparatory procedures, which are inconvenient to the patient, and to dispense with duplicating examination in different positions.

The apparatus for carrying out at least one embodiment of the method accordingly has a memory unit for storage of a plurality of volume data records, recorded by use of a CT scanner, of an area of the bowel of interest, a processing unit for the volume data records which, from a first of the stored volume data records or from a data record derived from this, identifies and suitably modifies voxels relating to a bowel content, in order to obtain a modified data record without visible bowel contents, and a visualization unit for visualization of the modified data record. In this case, the processing unit is designed such that it identifies at least some of the voxels relating to the bowel content on the basis of information about a local density and/or atomic number, which it calculates from data from the first and at least one further volume data record, taking account of different spectral distributions with which the volume data records have been recorded.

BRIEF DESCRIPTION OF THE DRAWINGS

The present method and the associated apparatus will be explained briefly once again in the following text using one example embodiment and in conjunction with the drawings, without any restriction to the scope of protection specified by the patent claims. In this case:

FIG. 2 shows, schematically, one example of the method procedure for an embodiment of the present method.

DETAILED DESCRIPTION OF THE EXAMPLE EMBODIMENTS

Figure 1:
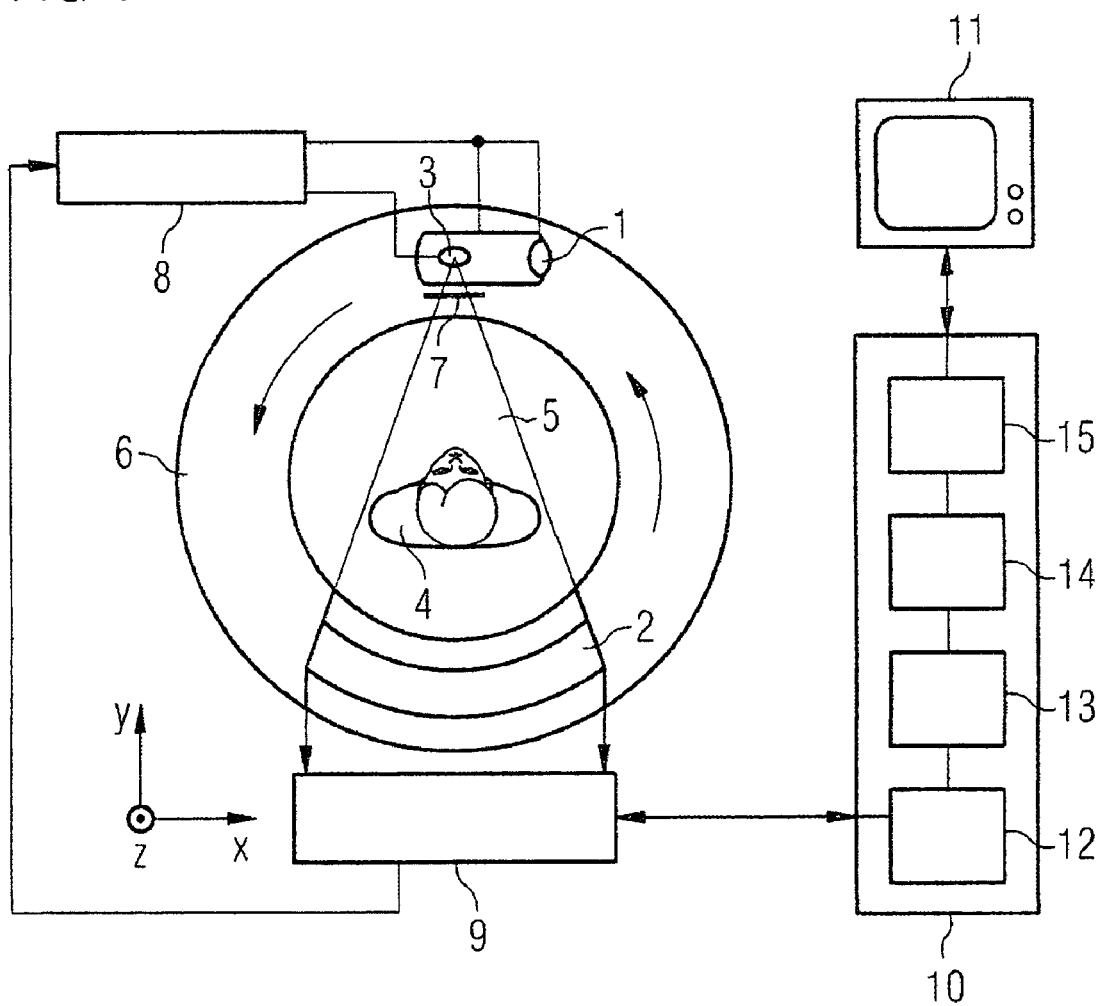
FIG. 1 shows a highly schematic illustration of a CT system with an apparatus according to an embodiment of the present invention.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows, highly schematically, one configuration of a CT scanner system having an apparatus designed according to an embodiment of the present invention. The CT scanner system has an X-ray source in the form of an X-ray tube 1, which emits a fan-shaped X-ray beam 5 in the direction of a row of detectors with X-ray detector elements 2. Both the X-ray tube 1 and the detector elements 2 are arranged on a rotating frame 6, the so-called gantry, which rotates continuously around a patient 4 during a measurement. The patient 4 lies on a patient couch, which is not illustrated in FIG. 1 but extends into the rotating frame 6.

The rotating frame 6 rotates on an x-y plane in a Cartesian coordinate system x-y-z which is indicated in FIG. 1. The patient couch can be moved along the z-axis, which corresponds to the slice thickness direction of the respective slices of the patient 4 to be displayed. The extent of the X-ray beam 5 in the z direction, in the present illustration the direction at right angles to the plane of the drawing, is predetermined on the one hand by the extent of the focus 3 on the rotating anode of the X-ray tube 1 and on the other hand by the shutter 7 which is arranged at the tube end and whose shutter opening can be moved in the z direction.

The X-ray tube 1 is supplied via a high-voltage generator 8 with a high voltage which can be set to at least two different high-voltage values in order to produce X-ray radiation with different spectral distributions. A controller 9 is used to drive the individual components of the CT scanner; in particular of the high-voltage generator 8, of the rotating frame 6, of the detector elements 2 and the patient couch, in order to record the measurement data.

The measurement data produced by the detector elements 2 is passed to the present apparatus, which is in the form of an image computer 10. The image computer 10 includes an image reconstruction unit 12 in which the image reconstruction process is carried out, in the present example the reconstruction of the volume data record from the measurement data. Each of the volume data records is temporally stored in the memory unit 13.

An image display of suitable views from the volume data record or from a data record which has been processed further by the processing unit 14 is provided by the visualization unit 15 on a monitor 11. In the present example, the processing unit 14 carries out the virtual bowel cleaning process on the basis of the method according to an embodiment of the invention. For this purpose, it accesses the memory unit 13, in which the volume data records which have been recorded with different spectral distributions are stored.

In the present example embodiment, virtual CT colonography is carried out with virtual bowel cleaning, in which case the patient has been given food enriched with contrast agent in a time period from 1 to 2 days before the examination. Two CT volume records of the bowel are then recorded, with different spectral distributions, successively by the CT scanner. The two different spectral distributions S1/S2 are obtained by way of different settings of the tube voltage for the CT scanner. Image reconstruction based on the recorded raw data results for each of the records in an attenuation value distribution $\mu_1(x,y,z)$ or $\mu_2(x,y,z)$ of the attenuation coefficient $\mu$ on which the respective volume data record is based.

First of all, the bowel is segmented from the first volume data record on the basis of the CT attenuation values of the area filled with contrast agent. The CT attenuation values in this area are between 300 and 500 HU (Hounsfield Units), depending on the contrast agent, so that this area can be separated without any problems from the other image areas by means of a threshold-value method. After this segmentation of the area filled with contrast agent, this area is widened in all directions in order in this way also to include the bowel wall in the segmented area. This segmented section is then processed further as a derived data record, using an embodiment of the present method.

An atomic number distribution Z (x,y,z) as well as a density distribution ρ (x,y,z) are then obtained from the volume data records for the individual voxels in this segmented data record by computer-aided transformation of the attenuation value distributions $\mu_1$ and $\mu_2$, respectively. This can be done using the technique that is known from DE 101 43 131 A1.

On the basis of this additional density and atomic number information, a distinction is then drawn for each voxel in the segmented data record as to whether that voxel represents bowel content material or bowel wall material. All of the voxels which represent the bowel content are identified in this way. Finally, the voxels which represent the bowel content are modified so that those areas which belong to the bowel content are eliminated in a subsequent image display of the data record that has been processed further in this way, that is to say they appear dark in the CT image. Additional image processing steps may, of course, also be carried out in this case, for example smoothing of transitions that occur in order to improve the image result.

The volume data record produced in this way is then visualized in a suitable manner in order to display the bowel without the bowel content to the user.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for virtual bowel cleaning, comprising:
   producing a first volume data record, recorded by a CT scanner, of at least one area of interest of the bowel;
   identifying voxels relating to a bowel content and suitably modifying the identified voxels in at least one of the first volume data record and a data record derived from the first volume data record;
   producing at least one further volume data record of the area of interest, which was recorded by the CT scanner with a different spectral distribution than the first volume data record; and
   identifying at least some of the voxels relating to the bowel content on the basis of a difference in at least one of a density and an atomic number between the bowel content and the bowel wall, the at least one of the density and atomic number being obtained from data in the first and the further volume data record taking account of the different spectral distributions; and
   producing a modified data record which includes the bowel without any visible bowel content and visualizing the modified data record.

2. The method as claimed in claim 1, wherein some of the voxels relating to the bowel content are identified on the basis of CT attenuation values.

3. The method as claimed in claim 2, wherein the area of the bowel of interest is segmented before identification of those voxels from the first volume data record which relate to the bowel content.

4. The method as claimed in claim 1, wherein the area of the bowel of interest is segmented before identification of those voxels from the first volume data record which relate to the bowel content.

5. An apparatus for virtual bowel cleaning, comprising:
   a memory unit to store a plurality of volume data records, recorded by a CT scanner, of an area of the bowel of interest;
   a processing unit for the volume data records to, from at least one of a first of the stored volume data records and a data record derived from a first of the stored volume data records, identify and suitably modify voxels relating to a bowel content in order to obtain a modified data record which includes the bowel without visible bowel contents; and
   a visualization unit to visualize the modified data record, wherein the processing unit is designed to identify at least some of the voxels relating to the bowel content based on a difference in at least one of a density and an atomic number between the bowel content and the bowel wall, the difference between the at least one of the density and the atomic number being calculated from data from the first and at least one further volume data record, taking account of different spectral distributions with which the volume data records have been recorded.

6. The apparatus as claimed in claim 5, wherein the processing unit is designed such that it identifies some of the voxels relating to the bowel content on the basis of CT attenuation values.

7. The apparatus as claimed in claim 6, wherein the processing unit is designed such that it segments the area of the bowel of interest before the identification of those voxels from the first volume data record which relate to the bowel content.

8. The apparatus as claimed in claim 5, wherein the processing unit is designed such that it segments the area of the bowel of interest before the identification of those voxels from the first volume data record which relate to the bowel content.

* * * * *